United States Patent [19]

Gaffar

[11] 4,370,314

[45] Jan. 25, 1983

[54] ORAL COMPOSITION CONTAINING ANTIBACTERIAL AGENT

[75] Inventor: Abdul Gaffar, Somerset, N.J.

[73] Assignee: Colgate-Palmolive Company, New York, N.Y.

[21] Appl. No.: 760,202

[22] Filed: Jan. 17, 1977

Related U.S. Application Data

[63] Continuation-in-part of Ser. No. 638,240, Dec. 8, 1975, abandoned.

[51] Int. Cl.³ ............................................. A61K 7/22
[52] U.S. Cl. ......................................................... 424/54
[58] Field of Search ................... 252/106; 424/49–58

[56] References Cited

U.S. PATENT DOCUMENTS

| | | | |
|---|---|---|---|
| 2,519,841 | 8/1950 | Macmahon | 252/106 |
| 2,541,248 | 2/1951 | Hibbs | 252/106 |
| 2,702,774 | 2/1955 | Staynor | 424/329 |
| 2,921,885 | 1/1960 | Bouchal et al. | 424/54 |
| 3,004,897 | 10/1961 | Shore | 424/54 |
| 3,507,796 | 4/1970 | Voss | 252/106 |
| 3,518,343 | 6/1970 | Welsh et al. | 424/44 |
| 3,591,675 | 7/1971 | Brilliant | 424/54 |
| 3,629,468 | 12/1971 | Anderson | 424/44 |
| 3,671,644 | 6/1972 | Irani et al. | 424/346 |
| 3,836,669 | 9/1974 | Dakian | 252/106 |

*Primary Examiner*—Shep K. Rose
*Attorney, Agent, or Firm*—Robert L. Stone; Murray M. Grill; Herbert S. Sylvester

[57] ABSTRACT

An antibacterial oral composition effective to promote oral hygiene containing a cationic quaternary ammonium antibacterial antiplaque agent and an additive which reduces staining of dental surfaces without unduly diminishing the antibacterial and antiplaque activity of the agent, which additive is an alkali metal hexametaphosphate or mixture thereof with alkali metal bicarbonate. Quaternary ammonium salts include benzethonium chloride and cetyl pyridinium chloride.

18 Claims, No Drawings

ORAL COMPOSITION CONTAINING ANTIBACTERIAL AGENT

This application is a continuation-in-part of application Ser. No. 638,240, filed Dec. 8, 1975 and now abandoned.

This invention relates to an antibacterial oral composition which promotes oral hygiene.

Cationic antibacterial materials are well known in the art. See, for instance the section on "Quaternary Ammonium and Related Compounds" in the article on "Antiseptics and Disinfectants" in Kirk-Othmer Encyclopedia of Chemical Technology 2nd Edition (Vol. 2, pgs. 632–635), incorporated herein by reference. Cationic materials which possess antibacterial activity (i.e., are germicides) are used against bacteria. As bacteria are present in the oral cavity and lead to plaque formation, cationic antibacterial agents have been used in oral compositions to counter plaque formation.

Among the most common of these antibacterial antiplaque quaternary ammonium compounds is benzethonium chloride, also known as Hyamine 1622 of di-isobutyl (phenoxyethoxyethyl dimethyl benzyl ammonium chloride). In an oral preparation this material is highly effective in promoting oral hygiene by reducing formation of dental plaque and calculus. Reduction of plaque and calculus is generally accompanied by reduction in caries formation and an improved peridontal health. Other cationic antibacterial agents of this type are those mentioned, for instance, in U.S. Pat. Nos. 2,984,639; 3,325,402; 3,703,583; and 3,431,208 and British Pat. No. 1,319,396.

Other antibacterial antiplaque quaternary ammonium compounds include those in which one of two of the substituents on the quaternary nitrogen has a carbon chain length (typically alkyl group) of some 8 to 20, typically 10 to 18, carbon atoms while the remaining substituents have a lower number of carbon atoms (typically alkyl or benzyl group), such as 1 to 7 carbon atoms, typically methyl or ethyl groups. Dodecyl trimethyl ammonium bromide, benzyl dimethyl stearyl ammonium chloride, cetyl pyridinium chloride and quaternized 5-amino-1,3-bis(2-ethylhexyl)-5-methyl hexahydro-pyrimidine are typical quaternary ammonium antibacterial agents.

The antibacterial antiplaque compound is preferably one which has an antibacterial acticity such that its phenol coefficient is well over 50, more preferably well above 100, such as above about 200 or more for S. aureus; for instance the phenol coefficient (A.O.A.C.) of benzethonium chloride is given by the manufacturer as 410, for S. aureus. The cationic antibacterial agent will generally be a monomeric (or possibly dimeric) material of molecular weight well below 2,000, such as less than about 1,000. It is, however, within the broader scope of the invention to employ a polymeric cationic quaternized antibacterial agent. The cationic antibacterial agent is preferably supplied in the form of an orally acceptable salt thereof, such as the chloride, bromide, sulfate, alkyl sulfonate such as methyl sulfonate and ethyl sulfonate, phenylsulfonate, such as p-methylphenyl sulfonate, nitrite, acetate, gluconate, etc.

The foregoing antibacterial agents are desirable and useful in the practice of this invention. Other conventional antibacterial agents such as water-soluble salts of the bis-biguanides, typical examples of which are 1,6-di(p-chlorophenyl biguanido) hexane and 1,6-bis(2-ethyl-hexyl biguanido)hexane, known as chlorhexidine, and alexidine, respectively, are precipitated by the anti-stain additives of the invention and are therefore, not a part thereof.

Anti-stain additives are desirable since although the cationic quaternary ammonium antibacterial agents effectively promote oral hygiene, particularly by removing plaque, their use has been observed to lead to staining of dental surfaces or discoloration.

The reason for the formation of such dental stain has not been clearly established. However, human dental enamel contains a high proportion (about 95%) of hydroxyapatite which includes $Ca^{+2}$ and $PO_4^{-3}$ ions. In the absence of dental plaque additional $Ca^{+2}$ and $PO_4^{-3}$, particularly from saliva, can be deposited on the enamel and such deposits can include color bodies which ultimately stain the tooth enamel as a calcified deposit thereon. It can be that as the cationic or long chain tertiary amine antibacterial agents remove plaque they also denature protein from saliva in the oral environment and the denatured protein can then act as a nucleating agent which is deposited on the stains or discolors tooth enamel.

It is an advantage of this invention that an antistain additive is provided which prevents staining of dental enamel without substantially adversely affecting antibacterial and antiplaque activity of a cationic quaternary ammonium or antibacterial agent. Other advantages will be apparent from consideration of the following disclosure.

In accordance with certain of its aspects this invention relates to an oral composition comprising an aqueous-humectant oral vehicle, a nitrogen-containing cationic quaternary ammonium antimicrobial agent and an additive which reduces staining of dental surfaces consisting essentially of an additive selected from the group consisting of alkali metal hexametaphosphate and mixture of alkali metal hexametaphosphate and alkali metal bicarbonate.

Antibacterial agents which are cationic quaternary ammonium germicides which may be employed in the particles of this invention are described above. They are typically employed in amounts such that the oral product contains between about 0.001% and 15% by weight of the agent. Preferably for desired levels of antiplaque effect, the finished oral product contains about 0.01 to about 5%, and most preferably about 0.025% to 1.0% by weight of agent.

The stain which generally occurs on dental enamel is unexpectedly prevented when the alkali metal e.g., sodium, potassium, ammonium etc., hexametaphosphate or hexametaphosphate-bicarbonate mixture is employed. These agents are particularly desirable. Other alkali metal salts such as sodium pyrophosphate and sodium tripolyphosphate lack hydrolytic stability and do not substantially reduce dental stain.

The anti-stain agents are alkali metal hexametaphosphate or mixture thereof with alkali bicarbonate. The preferred alkali metal is sodium. Substantial antibacterial activity remains when the stain reducing agents are employed.

The concentrations of alkali metal hexametaphosphate and alkali metal metaphosphate-alklai metal bicarbonate mixture in the oral compositions can vary widely. There is no upper limit on the amount that can be utilized except as dictated by factors such as incompatibility with the vehicle. Generally, when alkali metal bicarbonate is utilized it is in concentrations of from about 2 to about 40% by weight; typically about 2.5–5%. Further, generally, alkali metal hexametaphosphate is utilized in concentrations of from about 0.025% to about 5% by weight, typically about 0.025–2%. Desirably, a mouthwash contains up to about 10% by weight of the anti-stain agent and dentifrice compositions, topical solutions and prophylactic pastes (which are administered professionally) contain up to about 15% by weight, preferably up to about 12% by weight, of the anti-stain agent. Most preferably, the anti-stain agent is present in a molar excess to the amount of antibacterial antiplaque agent, in order to best prevent staining by the antibacterial antiplaque agent.

In certain highly preferred forms of the invention the oral composition may be substantially liquid in character, such as a mouthwash or rinse. In such a preparation the vehicle is typically aqueous-humectant and also generally includes water-alcohol mixture. Generally, the ratio of water to alcohol is in the range of from about 1:1 to about 20:1 preferably from 3:1 to 20:1 and most preferably about 17:3, by weight. The total amount of water-alcohol mixture in this type of preparation is typically in the range of from about 70% to about 99.9% by weight of the preparation. The pH of such liquid prepatations is generally in the range of from about 7 to about 9.5 and typically from about about 7.0 to 8.7.

Such liquid oral preparations may also contain a surface active agent and/or a fluorine-providing compound.

In certain other desirable forms of this invention, the oral composition may be substantially solid or pasty in character, such as toothpowder, a dental tablet or a toothpaste or dental cream. Such compositions typically have a pH like that of a mouthwash or mouthrinse. The vehicle of such solid or pasty oral preparations contains polishing material. Examples of polishing material are water-soluble sodium metaphosphate, potassium metaphosphate, tricalcium phosphate, dihydrated calcium phosphate, anhydrous dicalcium phosphate, calcium pyrophosphate, magnesium, alumina, hydrated alumina, aluminum silicate, zirconium silicate, silica, bentonite, and mixtures thereof. Preferred polishing materials include crystalline silica having particle sizes of up to 5 microns, a mean particle size of up to 1.1 microns, and a surface area of up to 50,000 cm$^2$/gm. silica gel, complex amorphorus alkali metal aluminosilicate and hydrated alumina.

Alumina, particularly the hydrated alumina sold by Alcoa as C333, which has an alumina content of 64.9% by weight, a silica content of 0.008%, a ferric oxide content of 0.003%, and a moisture content of 0.37% at 110° C., and which has a specific gravity of 2.42 and a particle size such that 100% of the particles are less than 50 microns and 84% of the particles are less than 20 microns, is particularly desirable.

When visually clear gels are employed, a polishing agent of colloidal silica, such as those sold under the trademark SYLOID as Syloid 72 and Syloid 74 or under the trademark SANTOCEL as Santocel 100 and alkali metal aluminosilicate complexes are particularly useful, since they have refractive indices close to the refractive indices of gelling agent-liquid (including water and/or humectant) systems commonly used in dentifrices.

Many of the so called "water-insoluble" polishing materials are anionic in character and also include small amounts of soluble material. Thus, insoluble sodium metaphosphate may be formed in any suitable manner, as illustrated by Thorpe's *Dictionary of Applied Chemistry*, Volume 9, 4th Edition, pp. 510–511. The forms of insoluble sodium metaphosphate known as Madrell's salt and Kurrol's salt are further examples of suitable materials. These metaphosphate salts exhibit a minute solubility in water, and therefore are commonly referred to as insoluble metaphosphates. There is present therein a minor amount of soluble phosphate material as impurities, usually a few percent such as up to 4% by weight. The amount of soluble phosphate material, which is believed to include a soluble sodium trimetaphosphate in the case of insoluble sodium metaphosphate, may be reduced by washing with water if desired. The insoluble alkali metal metaphosphate is typically employed in powder form of a particle size such that no more than 1% of the material is larger than 37 microns.

The polishing material is generally present in amounts ranging from about 20% to about 99% by weight of the oral preparation. Preferably, it is present in amounts ranging from about 20% to about 75% in toothpaste, and from about 70% to about 99% in toothpowder.

In the preparation of toothpowders, it is usually sufficient to admix mechanically, e.g., by milling, the various solid ingredients in appropriate quantities and particle sizes.

In pasty oral preparations the combination of the antibacterial antiplaque agent and anti-stain compound should be compatible with the other components of the preparation. Thus, in a toothpaste, the liquid vehicle may comprise water and humectant, typically in an amount ranging from about 10% to about 90% by weight of the preparation. Glycerine, sorbitol, or polyethylene glycol may also be present as humectants or binders. Particularly advantageous liquid ingredients comprise mixtures of water, glycerine and sorbitol.

In clear gels where the refractive index is an important consideration, about 3–30% by weight of water, 0 to about 80% by weight of glycerine, and about 20–80% by weight of sorbitol is preferably employed. A gelling agent, such as natural or synthetic gums or gum-like materials, typically Irish Moss, sodium carboxymethylcellulose, methyl cellulose, or hydroxyethyl cellulose, may be employed. Other gelling agents which may be employed include gum tragacanth, polyvinylpyrrolidone and starch. They are usually present in toothpaste in an amount up to 10% by weight, preferably in the range of from about 0.5% to about 5%. The preferred gelling agents are methyl cellulose and hydroxyethyl cellulose. In a toothpaste or gel, the liquids and solids are proportioned to form a creamy or gelled mass which is extrudable from a pressurized container or from a collapsible, e.g., aluminum or lead, tube.

The solid or pasty oral preparation which typically has a pH measured on a 20% slurry of about 7 to about 9.5 and generally about 7.0 to about 8.7, may also contain a surface active agent and/or a fluorine-providing compounds.

It will be understood that, as is conventional, the oral preparations are to be sold or otherwise distributed in suitably labelled packages. Thus a jar of mouthrinse will have a label describing it, in substance, as a mouthrinse or mouthwash and having directions for its use; and a toothpaste will usually be in a collapsible tube, typically aluminum or lined lead, or other squeeze dispenser for metering out the contents, having a label describing it, in substance, as a toothpaste or dental cream.

In oral compositions such as mouthrinses and toothpastes, a surfactant is often present, e.g., to promote foaming. It will be understood that it is preferable to employ nonionic surfactants rather than their anionic counterparts. Examples of water-soluble nonionic surfactants are condensation products of ethyleneoxide with various compounds reactive therewith having long hydrophobic chains (e.g., aliphatic chains of 12 to 20 carbon atoms) which condensation products ("ethoxamers") have hydrophobic polyoxyethylene moieties, such as condensation products of ethylene oxide and fatty acids, fatty alcohols, fatty amides, including alcohols such as sorbitan monostearate or polypropyleneoxide (that is Pluronic materials).

In certain forms of this invention a fluorine-providing compound is present in the oral preparation. These compounds may be slightly soluble in water or may be fully water-soluble. They are characterized by their ability to release fluoride ions in water and by substantial freedom from reaction with other compounds of the oral preparation. Among these materials are inorganic fluoride salts, such as soluble alkali metal, alkaline earth metal and heavy metal salts, for example, sodium fluoride, potassium fluoride, ammonium fluoride, lead fluoride, a copper fluoride such as cuprous fluoride, zinc fluoride, a tin fluoride such as stannic fluoride or stannous chlorofluoride, barium fluoride, sodium fluorosilicate, ammonium fluorosilicate, sodium fluorozirconate, sodium monofluorophosphate, aluminum mono- and di-fluorophosphate, and fluorinated sodium calcium pyrophosphate. Alkali metal and tin fluorides, such as sodium and stannous fluorides, sodium monofluorophosphate and mixtures thereof, are preferred.

The amount of the fluorine-providing compound is dependent to some extent upon the type of compound, its solubility and the type of oral preparation, but it must be a nontoxic amount. In a solid oral preparation, such as a toothpaste or toothpowder, an amount of such compound which releases a maximum of 1% by weight of the preparation is considered satisfactory. Any suitable minimum amount of such compound may be used, but it is preferable to employ sufficient compound to release from 0.005% to 1%, and preferably about 0.1% of fluoride ion. Typically, in the cases of alkali metal fluorides and stannous fluoride, this component is present in an amount up to 2% by weight, based on the weight of the preparation, and preferably in the range of from 0.05% to 1%. In the case of sodium monofluorophosphate, the compound may be present in an amount up to 7.6% by weight more typically 0.76%.

In a liquid oral preparation such as a mouthwash, the fluorine-providing compound is typically present in an amount sufficient to release up to 0.13%, preferably from 0.0013% to 0.1% and most preferably from 0.0013% to 0.05%, by weight, of fluoride ion.

Various other materials may be incorporated in the oral preparations of this invention. Examples of whitening agents, preservatives, silicones, chlorophyll compounds, and ammoniated material such as urea, diammonium phosphate, and mixtures thereof. These adjuvants, where present, are incorporated in the preparations in amounts which do not substantially adversely affect the properties and characteristics desired.

Any suitable flavoring of sweetening material may also be employed. Examples of suitable flavoring constituents are flavoring oils, e.g., oils of spearmint, peppermint, wintergreen, sassafras, clove, sage, eucalyptus, marjoram, cinnamon, lemon, and orange, and methyl salicylate. Suitable sweetening agents include sucrose, lactose, maltose, sorbitol, sodium cyclamate, perillartine, and saccharin. Suitably, flavor and sweetening agents may together comprise from 0.01% to 5% or more of the preparation.

Oral preparations of the invention may be prepared by dispersing the cationic quaternary ammonium antibacterial anti-plaque agent and the alkali metal salt anti-staining agent in an oral vehicle which typically includes water.

For instance, a mouthrinse or mouthwash may be prepared by mixing an aqueous-humectant vehicle, e.g., containing ethanol, water, flavoring oil, nonionic surfactant and humectant with cationic antibacterial agent, such as benzethonium chloride or cetyl pyridinium chloride, and then adding the alkali metal anti-staining compound and additional water as desired. It is desirable to add the anti-staining compound after the other ingredients are contacted with each other.

A toothpaste may be prepared by forming a gel with water, humectant, gum or thickener such as hydroxyethyl cellulose, sweetener and adding thereto polishing agent, flavor, antibacterial agent, such as benzenethonium chloride or cetyl pyridinium chloride, and additional water, followed by addition of flavoring oil and the anti-staining compound. It is preferable to add the anti-staining compound after the other components are contacted with each other.

In the practice of this invention an oral composition such as a mouthwash or toothpaste containing cationic quaternary ammonium antibacterial antiplaque agent in amount effective to promote oral hygiene and anti-staining alkali metal compound in amount effective to reduce staining of dental surfaces otherwise resulting from the presence of the antibacterial antiplaque agent is applied regularly to dental enamel, preferably from about 5 times per week to about 3 times daily.

The following specific examples are further illustrative of the nature of the present invention; but it is understood that the invention is not limited thereto. The compositions are prepared in the usual manner and all amounts of the various ingredients are by weight unless otherwise indicated.

EXAMPLE 1

Mouthwashes of the following formula are prepared:

|  | Parts |
| --- | --- |
| Flavor | 0.073 |
| Ethanol | 5 |
| Pluronic F-108 | 3 |
| Glycerine | 10 |
| Benzethonium chloride | 0.075 |
| Sodium saccharin | 0.03 |
| Sodium hexametaphosphate | As indicated |
| Sodium bicarbonate | As indicated |
| Water | Q.S. to 100 |

The mouthwashes contain as anti-staining additive, sodium hexametaphosphate or a mixture of sodium hexametaphosphate and sodium bicarbonate in the amounts indicated. The pH of each mouthwash is also set forth.

| Mouthwash | Additive | Parts | pH |
|---|---|---|---|
| (a) | None | | 7.1 |
| (b) | Sodium hexametaphosphate | 0.05 | 7.2 |
| (c) | Sodium hexametaphosphate | 0.1 | 7.1 |
| (d) | Sodium hexametaphosphate | 0.5 | 7.0 |
| (e) | Sodium hexametaphosphate | 1.0 | 7.0 |
| (f) | Sodium hexametaphosphate | 0.05 | 8.2 |
| | Sodium bicarbonate | 2.5 | |
| (g) | Sodium hexametaphosphate | 0.025 | 8.7 |
| | Sodium bicarbonate | 2.5 | |
| (h) | Sodium hexametaphosphate | 0.25 | 8.1 |
| | Sodium bicarbonate | 2.5 | |

The mouthwashes are clear. When no sodium bicarbonate is present initial cloudiness can be present which disappears upon standing.

The antiplaque activity and staining levels of mouthwashes of the invention and mouthwash (a) are determined.

Tests are made of the ability of the compositions to inhibit in vitro plaque formation by allowing plaque to form (for 48 hours at 37° C.) on the surfaces of cleared and pumiced teeth in a preinoculated sucrose broth containing Strep mutans. The pre-grown plaque is then immersed in the test composition and rinsed with a buffer 1-5 times for one minute each. The teeth carrying the plaque are then transferred to a sucrose broth containing 1 mg/100 ml of bromocresol green indicator and incubated at 37° C. anaerobically for 18 hours. An antibacterial compound is considered effective if the indicator does not turn yellow (which begins when pH reaches 5.5) and there is no further growth of the plaque as judged by the increase in turbidity. It is found that on the clean teeth, plaque formation and plaque growth are effectively inhibited.

The tooth staining characteristics of the composition are tested by slurrying hydroxylapatite with salivary protein and acetaldehyde and a pH 7 phosphate buffer. The mixture is shaken at 37° C. until a light brown color is formed, which colored material is separated.

Color levels are determined on a Gardner Color Difference Meter before and after the test composition is applied to the colored material.

All mouthwashes (a)-(h) remain active after five rinses with the buffer and inhibit three day plaque growth.

Thus, it is observed that the additive does not unduly reduce the in vitro antiplaque activity of benzethonium chloride.

The anti-stain results are as follows for mouthwashes (a)-(h):

| Mouthwash | Reflectance | Reflectance Difference |
|---|---|---|
| (a) (control) | 42.0 | |
| (b) | 65.0 | 23.0 |
| (c) | 70.0 | 28.0 |
| (d) | 75.0 | 33.0 |
| (e) | 75.0 | 33.0 |
| (f) | 73.0 | 31.0 |
| (g) | 65.0 | 23.0 |
| (h) | 75.0 | 33.0 |

Thus, it is observed that the additive substantially reduces staining by benzethonium chloride.

When similar mouthwashes are formulated except that 0.1 part of each of the bis-biguanido water-soluble salts (based on the free base) 1,6-bi-(p-chlorophenyl biguanido) hexane and 1,6-bis-(2-ethylhexyl biguanido) hexane are employed as cationic antibacterial agents instead of benzethonium chloride, the antibacterial agent precipitates, activity is diminished and plaque growth and acid production are less inhibited.

EXAMPLE 2

Mouthwashes similar to those of Example 1 are prepared except that 0.5 parts of cetyl pyridinium chloride are employed instead of benzethonium chloride. These mouthwashes are or become clear and are active against plaque in vitro and inhibit plaque growth and acid as do the corresponding mouthwashes without anti-staining additive. In the anti-stain test reduced stain levels are obtained when the hexametaphosphate salt, the bicarbonate salt and mixtures thereof are present than when they are absent.

EXAMPLE 3

The following antiplaque reduced staining toothpastes are prepared:

| | Parts | Parts |
|---|---|---|
| Hydrated Alumina | 30 | 30 |
| Glycerine | 16 | 16 |
| Sorbitol (70%) | 6 | 6 |
| Pluronic F-108 | 3 | 3 |
| Hydroxyethyl cellulose | 1.2 | 1.2 |
| Benzethonium chloride | 0.5 | — |
| Cetyl pyridinium chloride | — | 0.5 |
| Sodium hexametaphosphate | 7 | 2 |
| Sodium bicarbonate | — | 10 |
| Sodium saccharin | 0.17 | 0.17 |
| Flavor | 0.8 | 0.8 |
| Water | Q.S. to 100 | Q.S to 100 |

EXAMPLE 4

The following mouthwashes are prepared and tested on humans:

| | Parts | | |
|---|---|---|---|
| Components | (a) | (b) | (c) |
| Flavor | 0.073 | 0.073 | 0.073 |
| Ethanol | 5 | 5 | 5 |
| Pluronic F-108 | 3 | 3 | 3 |
| Glycerine | 10 | 10 | 10 |
| Benzethonium chloride | — | 0.075 | 0.075 |
| Sodium hexametaphosphate | — | — | 1 |
| Sodium bicarbonate | — | — | 5 |
| Sodium saccharin | 0.03 | 0.03 | 0.03 |
| Water | Q.S. to 100 | Q.S. to 100 | Q.S. to 100 |

Three groups of twenty-five people in each group use each of mouthwashes (a), (b) and (c). Each person has at least 20 teeth and at least 9 front teeth. Thorough dental prophylaxis is given before the start of the test to remove existing soft and hard deposits. 15 cc of the mouthwash is used by each subject twice a day for one minute each time for 6 weeks. The following results are observed:

| Group | Mean Stain Per Tooth | % Change | Mean Plaque Per Tooth | % Change |
|---|---|---|---|---|
| (a) Placebo | 0.65 | | 0.80 | |
| (b) Control | 3.02 | 364 | 0.50 | 37.5 |

-continued

| Group | Mean Stain Per Tooth | % Change | Mean Plaque Per Tooth | % Change |
|---|---|---|---|---|
| (c) Additive | 1.19 | 83 | 0.60 | 25 |

Thus, both the control (b) and the additive (c) mouthwashes reduce plaque compared to the control, while substantially less stain forms with the additive, mouthwash (c) than with the control mouthwash (b).

The mean stain per tooth is calculated from the intensity of the stain on a particular tooth: 0 being none; 1 being ¼ of tooth; 2 being ½ of tooth; 3 being ¾ of tooth; and 4 being entire tooth. The mean plaque per tooth is determined from the extent plaque present on a particular tooth, observed with a disclosing solution: 0 being none; 1 being ¼ of tooth; 2 being ½ of tooth; 3 being ¾ of tooth; and 4 being entire tooth.

It will be apparent to one skilled in the art that modifications of the above examples may be made thereto.

I claim:

1. A packaged oral composition comprising an aqueous-humectant oral vehicle, a nitrogen-containing quaternary ammonium antibacterial antiplaque agent whose use has been observed to lead to staining of dental surfaces and an additive which reduces such staining consisting essentially of an additive selected from the group consisting of alkali metal hexametaphosphate and mixture of alkali metal hexametaphosphate and alkali metal bicarbonate.

2. The oral composition of claim 1 wherein said nitrogen containing antibacterial antiplaque agent is present in amount to provide about 0.001% to about 15% by weight based on the free base form of said agent and said alkali metal hexametaphosphate is present in amount of at least about 0.025% by weight.

3. The packaged oral composition of claim 1 wherein said nitrogen containing antibacterial antiplaque agent is present in amount to provide about 0.001% to about 15% by weight based on the free base form of said agent and said alkali metal hexametaphosphate is present in amount of at least about 0.025% by weight and at least about 2% of alkali metal bicarbonate is present.

4. The packaged oral composition of claim 1 wherein said nitrogen containing antibacterial antiplaque agent is present in an amount of about 0.01% to about 5% by weight based on the free base form of said agent and said additive is present in a molar excess relative to said agent.

5. The packaged oral composition of claim 1 wherein said antibacterial antiplaque agent is benzethonium chloride.

6. The packaged oral composition of claim 1 wherein said antibacterial antiplaque agent is a quaternary ammonium compound containing 1 to 2 alkyl groups of 8 to 20 carbon atoms.

7. The packaged oral composition of claim 6 wherein said antibacterial antiplaque agent is cetyl pyridinium chloride.

8. The packaged oral composition of claim 2 wherein said alkali metal hexametaphosphate is sodium hexametaphosphate.

9. The packaged oral composition of claim 3 wherein said alkali metal hexametaphosphate is sodium hexametaphosphate and said alkali metal bicarbonate is sodium bicarbonate.

10. The packaged oral composition of claim 1 wherein said aqueous-humectant vehicle includes alcohol and said composition is a mouthwash of pH of about 7 to about 9.5.

11. The packaged oral composition of claim 1 wherein said aqueous-humectant vehicle comprises a gelling agent and a dentally acceptable polishing material is also present and said composition is a toothpaste of pH of about 7 to about 9.5.

12. A mouthwash comprising an aqueous-humectant alcohol vehicle, about 0.01 to about 5.0% based on its free base weight of benzethonium chloride and about 0.025 to about 2% by weight of sodium hexametaphosphate.

13. A mouthwash comprising an aqueous-humectant alcohol vehicle, about 0.01 to about 5.0% based on its free base weight of benzethonium chloride and about 0.025 to about 2% by weight of sodium hexametaphosphate and about 2.5% to about 5% by weight of sodium bicarbonate.

14. A method comprising treating the oral cavity with a composition as defined in claim 1.

15. The packaged oral composition of claim 8 wherein said antibacterial antiplaque agent is benzethonium chloride.

16. The packaged oral composition of claim 8 wherein said antibacterial antiplaque agent is cetyl pyridinium chloride.

17. The packaged oral composition of claim 9 wherein said antibacterial antiplaque agent is benzethonium chloride.

18. The packaged oral composition of claim 9 wherein said antibacterial antiplaque agent is cetyl pyridinium chloride.

* * * * *